United States Patent [19]

Capobianco et al.

[11] Patent Number: 4,963,826
[45] Date of Patent: Oct. 16, 1990

[54] REFERENCE STANDARD BLOCK FOR USE IN NONDESTRUCTIVE TEST PROBE CALIBRATION AND METHOD OF MANUFACTURE THEREOF

[75] Inventors: Thomas E. Capobianco, Arvada; William P. Dubé, Denver, both of Colo.; Kenneth W. Fizer, Virginia Beach, Va.

[73] Assignee: The United States of America as represented by the Secretary of Commerce, Washington, D.C.

[21] Appl. No.: 381,553

[22] Filed: Jul. 18, 1989

[51] Int. Cl.$^5$ ............................................. G01R 35/00
[52] U.S. Cl. ..................................... 324/202; 72/377; 73/1 R
[58] Field of Search ........................ 324/202; 73/1 R; 72/377

[56] References Cited

U.S. PATENT DOCUMENTS

| 2,463,580 | 3/1949 | Warshyk et al. ................. 72/377 X |
| 2,936,520 | 5/1960 | Sternberg ......................... 72/377 X |
| 3,582,772 | 6/1971 | Hammer . |
| 3,718,315 | 2/1973 | Rogel et al. . |
| 4,000,009 | 12/1976 | Chatfield . |
| 4,172,855 | 10/1979 | Marsh . |
| 4,203,315 | 5/1980 | Vieu et al. . |
| 4,418,315 | 11/1983 | Edwards et al. . |
| 4,425,545 | 1/1984 | Scalese . |
| 4,558,585 | 12/1985 | Berry, Jr. . |
| 4,704,892 | 11/1987 | Tarnai . |

FOREIGN PATENT DOCUMENTS

| 2837746 | 10/1979 | Fed. Rep. of Germany . |
| 741136 | 6/1980 | U.S.S.R. . |
| 1018001A | 5/1983 | U.S.S.R. . |

OTHER PUBLICATIONS

J. C. Moulder et al., "Uniform Field Eddy Current Probe: Experimentation and Inversion for Realistic Flaws", Review of Progress in Quantitative Nondestructive Evaluation, vol. 6A, pp. 601–610, Plenum Press, New York, New York, 1987.
"Aluminum Standards and Data 1984", The Aluminum Association, pp. 54–58, Washington, D.C., 1984.
B. A. Auld et al., "Semi-Elliptical Surface Flaw EC Interaction and Inversion: Theory", Review of Progress in Quantitative Nondestructive Evaluation, vol. 5A, pp. 383–393, Plenum Press, New York, New York, 1986.
A. R. Jones, "Eddy Current Meter Standards-How Good Are They", Materials Evaluation, pp. 37–42 (Nov. 1977).
T. E. Capobianco et al., "Standard Flaws for Eddy Current Probe Characterization", National Institute of Standards and Technology, Electromagnetic Technology Division, Boulder, Colorado, Aug. 4, 1988, pp. 1–8.
W. D. Rummel et al., "Assessment of Eddy Current Probe Interactions with Defect Geometry and Operating Parameter Variations", Review of Progress in Quantitative Nondestructive Evaluation, vol. 6A, pp. 705–712, Plenum Press, New York, New York, 1987.

Primary Examiner—Gerard R. Strecker
Assistant Examiner—Warren S. Edmonds
Attorney, Agent, or Firm—Thomas Zack; Alvin J. Englert; Paul C. Hashim

[57] ABSTRACT

A reference standard and a method for manufacturing a reference standard for use in calibrating an eddy current probe is disclosed. The reference standard is produced from a block of metal that is deformed by an indentation tool to provide a notch of prescribed dimensions. The reference standard is compressed along an axis substantially transverse to the longitudinal axis of the notch to substantially close the notch. A family of reference standards formed in this manner can be produced to calibrate an eddy current probe prior to use of the probe in evaluating metal components such as aircraft framework for the presence of fatigue cracks and the like.

20 Claims, 2 Drawing Sheets

REFERENCE STANDARD BLOCK FOR USE IN NONDESTRUCTIVE TEST PROBE CALIBRATION AND METHOD OF MANUFACTURE THEREOF

BACKGROUND OF THE INVENTION

1. Field of the Invention

The invention relates generally to a reference standard block and a method of manufacturing reference standard blocks for use in calibrating eddy current nondestructive testing probes. More particularly, the invention relates to reference standard blocks having superficial flaws that simulate fatigue cracks and a method of manufacturing such reference standard blocks.

2. Description of the Related Art

Eddy current probes have been used and accepted as a means for locating structural flaws such as fatigue cracks formed in metal structures during nondestructive testing or eddy current nondestructive evaluation (NDE). Fatigue cracks are generally of microscopic dimensions and usually do not form a void in the metal matrix in which they are found. These cracks are also generally called discontinuities, and can weaken the structural load-bearing capabilities of the metals in which they are formed. The detection of structural flaws is of particular significance to industries such as the air transportation industry, for cracks can develop in aircraft framework as a result of repeated aircraft pressurization/depressurization events, impact associated with aircraft landings, and possibly other operational procedures. Failure to detect the presence of such structural flaws and attend to their correction can present a considerable risk to the health and safety of the crew operating the aircraft, as well as to the persons and cargo carried thereby, particularly if a structural failure occurs while the aircraft is at altitude. For these reasons, testing procedures capable of detecting flaws such as cracks in aircraft framework that are not readily detectable by the unaided human eye are particularly desirable, for such procedures allow for the repair and/or replacement of components before a potentially harmful failure can occur.

Eddy current probes which are to be used to detect flaws such as fatigue cracks in structural members need to be calibrated with a specimen which simulates the type of fatigue crack anticipated to be found in the structural members under study. The reference standards which have been produced to date have many shortcomings in this regard and do not enable accurate calibration of eddy current probes for the detection of fatigue cracks and dislocations.

In general, eddy current testing works on the following principle. A high frequency alternating current is driven through a wire coil contained in the probe. This current produces an alternating magnetic field which emanates form the end of the coil. When the end of the coil is brought into proximity of a conducting material, the magnetic field induces circulating electric currents, known as eddy currents, in the material being tested. The presence of cracks or discontinuities in the test material will alter the pattern of the induced eddy currents and the associated magnetic field, thereby producing a change in the electrical parameters of the coil in the probe. These changes in electrical parameters are electronically manipulated into a useful form, such as a meter reading or a graphic display, thereby allowing for the identification and detection of flaws that may have otherwise been visually undetectable. One of the commonly measured electrical parameters is electrical impedance.

In order to optimize the accuracy of measurements obtained from eddy current nondestructive testing of structures, the eddy current device must first be calibrated to ensure that the measurement obtained during nondestructive testing can be properly interpreted. Eddy current probes are generally calibrated by using a reference standard or test block having formed therein a manufactured flaw such as a minute fissure of prescribed dimensions. A reference standard having a manufactured flaw of dimensions at least as large as the smallest flaw for which detection is sought during an inspection of a test structure is selected for probe calibration. Eddy current values as measured by a particular probe on the selected reference standard are compared to values produced by the probe on an actual flaw or fatigue crack in a part under test to provide an indication of the severity of the flaw.

Flaws of prescribed dimensions are formed in the reference standards usually through the use of milling equipment or electrical discharge machining (EDM). Reference standards in use to date have gained notoriety for being highly variable both dimensionally and in their eddy current response. At present, there are no specifications covering the production of artifact standards or blocks, and as a result there has been a proliferation of commercial and "homemade" calibration standard blocks of variable quality. The proliferation of these blocks has caused considerable confusion in the structural flaw testing field as to which calibration standard is appropriate in a given test situation.

Instruments that are sensitive to eddy current signal phase and amplitude are able to show considerable differences in phase between a relatively wide EDM notch or milled slot, and a naturally-produced fatigue crack. Saw cuts and relatively narrow EDM notches provide more reasonable flaw approximations for probe calibration incident to an inspection testing or comparatively large defects, but fatigue crack detection requires a more precise evaluation and calibration regimen, as fatigue cracks are generally of small dimensions and are therefore difficult to identify.

Naturally-produced fatigue cracks that have been identified in portions of previously studied structural members have been used to a limited extent for probe calibration purposes, but these fatigue cracks have proven to be difficult to use on a widespread, regular basis for several reasons: (1) they are difficult to reproduce; (2) the dimensions of the crack can change over time as crack tip stresses force the crack faces toward one another and into electrical contact; and (3) the precise dimensions of the crack are never actually known until the crack is broken apart and analyzed, thereby terminating further utility of the specimen as a probe calibration device.

A number of reference standards have been produced for calibrating eddy current probes and ultrasonic-vibration testing apparatus using a wide range of manufacturing techniques. For example, U.S. Pat. No. 4,203,315 discloses a reference block for nondestructive testing that includes a plurality of inserts fitted within a housing that defines the reference block. However, a metallurgical bond is formed between the inserts and the housing by a process that includes heat treatment. A principal limitation of this reference standard lies in the fact that the reference standard is formed with numerous substantive discontinuities by virtue of the inserts positioned within the specimen.

Another reference standard is disclosed in U.S. Pat. No. 4,704,892, which provides a control specimen having a plurality of cavities machined into a portion of the specimen. This reference, and the majority of the reference standards in the prior art, however, attempt to simulate defects in the surface of a specimen rather than flaws such as cracks which extend inwardly from the specimen surface.

In view of the foregoing limitations in the related art, it is clear that there exists a need for readily reproducible reference standard blocks that permit for the accurate and reliable calibration of eddy current probes prior to use of the probes in testing structural components for flaws such as cracks that are not detectable with the unassisted human eye.

SUMMARY OF THE INVENTION

In one embodiment of the invention, a reference standard block is manufactured by a method in which a block of metal is deformed with an indenter leaving a slot-like indentation or notch. Thereafter the reference standard is compressed along an axis substantially transverse to the longitudinal axis of the notch to substantially close the notch. A family of reference standards formed in the manner can be produced for use in calibrating an eddy current probe prior to use of the probe in evaluating metal components such as aircraft framework for the presence of fatigue cracks and the like. The reference standard blocks can also be annealed after compressing to remove work hardening caused by the indentation formation and compression. The blocks can be formed from an aluminum alloy that is heat treated after annealing in order to substantially return the aluminum alloy to its original temper.

In the preferred embodiment, the reference standard blocks are made from a 7075 aluminum alloy, as this is the alloy from which much aircraft framework is fabricated. However, in alternate embodiments, the family of reference standards can be manufactured from other metals and alloys to permit for proper calibration of the eddy current probe in accordance with the type of metal to be examined. For example, for eddy current probe examination of a structure manufactured from titanium or an alloy thereof, the probe is calibrated with one or more of a family of reference standards formed from titanium or the particular titanium alloy under examination. Any particular metal or metal alloy can be used in the manufacture of a family of reference standards for calibration of an eddy current probe used in the inspection of a structure manufactured from that particular metal or metal alloy.

BRIEF DESCRIPTION OF THE DRAWINGS

The various features and advantages of the subject invention will become more apparent from a reading of the following specification and drawings, in which.

DETAILED DESCRIPTION OF THE PREFERRED EMBODIMENT

Figure 1:
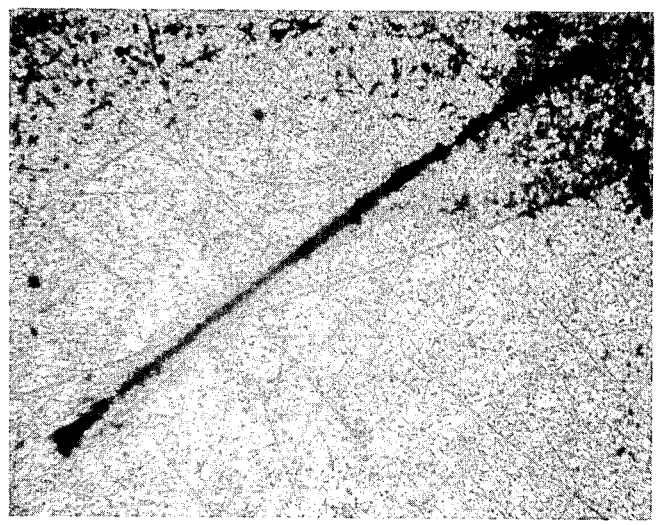
FIG. 1 is a photomicrograph of a top view of a slot indentation formed in an aluminum alloy reference standard block in accordance with the method of the subject invention, the slot indentation being magnified approximately 50X.

The subject invention provides an accurate and reliable reference standard block and method of block manufacture in which the block is provided with at least one fine crack or notch of a type that may not readily discernable with the unassisted human eye and that is exemplary of the type of cracks that have been observed to develop over time in objects such as the framework of military and commercial aircraft.

In the preferred embodiment of the present invention, a flaw similar to a fatigue crack is formed in an aluminum block with an indentation tool to form an indentation or notch that extends through the surface of the block. The indentation tool is preferably formed from stainless steel shim stock. In an alternate aspect of the preferred embodiment, the indentation can be formed by electrical discharge machining (EDM) or other machining methods. Following indentation formation, the block is compressed in a direction transverse to the long axis of the indentation in order to substantially close the indentation opening to form a discontinuity that extends into the interior of the block. The width of the discontinuity ranges from about 0.005 mm to about 0.10 mm. The compressed block is then annealed to relieve the effects of work hardening and heat treated to restore the block to a temper value approximate that of the original temper.

A variety of reference standard blocks were produced in accordance with the foregoing method of the invention and tested. The reference standards were formed so as to provide only one flaw per block. However, the following description of the invention is also applicable to the formation of a block having more than one flaw. The dimensions of each block tested was 3 in. $\times$ 3 in. $\times$ ⅜ in., and the dimensions of the notch formed in each tested block ranged from about 1 mm to about 20 mm in length.

Reference standard blocks in accordance with the invention were made from two different aluminum alloys. The feasibility of the method was evaluated using 6061 aluminum alloy. 7075 aluminum alloy was substituted for 6061 aluminum because the latter alloy is more commonly used in aerospace applications and has a more consistent grain structure. However, reference standard blocks in accordance with the invention can be made of any number of metals or alloys that can be processed by annealing, tempering, or other metal working processes. For instance, for nondestructive testing of a structure constructed of a titanium alloy, reference blocks are formed from that same titanium alloy to permit for proper probe calibration prior to examination of the structure under consideration.

In a first experiment, the data of which is set forth below at Table 1, the block indentations were formed with a number of different indenting tools each made from stainless steel shim stock. The work end of each tool was formed into one of a variety of configurations, including circular arcs, semi-circles and semi-ellipses. The work end of each tool was pressed into an annealed block of the aluminum alloy to form a single indentation in the block. Following block indentation, the block was annealed to remove the effects of cold working around the notch. The blocks were then compressed in a direction transverse to the longitudinal axis of the notch to substantially close the notch opening. Following block annealing, each block was heat treated in an attempt to return the material to a condition near its original T651 temper (ASTM standards) such as the T6 temper. Material condition throughout the process was tracked using a combination of hardness testing and eddy current measurements. The data obtained from three aluminum blocks processed in the foregoing manner is provided in Table 1, where "$R_B$" represents Rockwell B scale hardness number, "Mag. ($\Omega$)" represents the measured magnitude of the impedance (in ohms), and "phase (°)" indicates the phase angle in degrees of the measured impedance.

TABLE I

Rockwell B Scale Measurements and Eddy Current Impedance for Blocks formed from Aluminum Alloy 7075.

| Block | Prior to Processing | | | Following Processing | | |
|---|---|---|---|---|---|---|
| | Hardness ($R_B$) | Mag. ($\Omega$) | Phase (°) | Hardness ($R_B$) | Mag. ($\Omega$) | Phase (°) |
| A | 87.7 | 50.76 | 78.25 | 90.0 | 51.69 | 78.81 |
| B | 88.7 | 50.76 | 78.25 | 89.0 | 51.52 | 78.88 |
| C | 88.2 | 50.78 | 78.24 | 89.1 | 51.58 | 78.87 |

The differences illustrated in Table I between the measured magnitude of the impedance (Mag. ($\Omega$)) in the aluminum blocks prior to and following processing can be attributed to several possible causes. One possible cause can be attributed to the existence of several viable processing cycles that can be used for both the solution heat treating and the precipitation treatment of the aluminum blocks to restore the T6 level of temper, as set forth by data published by the Aluminum Association. Furthermore, the aluminum blocks prior to processing were of a T651 temper that were stress-relieved by stretching the alloy in the mill. This stress-relieving could not be replicated during the post-indentation processing steps performed in the lab. It is therefore possible that the differences in material properties post- and pre-processing that are noted in Table 1 could be explained as being a consequence of slightly different heat treating processes that were performed prior to and following material processing.

While differences existed in the pre- and post-processing of the aluminum blocks, it should be noted that these differences in the values listed in Table 1 amounted to less than 2% for the values of measured impedance, and only about 1% in the measured phase angle. This data indicates that despite the existence of slight differences in the aluminum alloy blocks prior to and following processing that may be attributable to the factors discussed above, the overall effect of the processing of the aluminum blocks has a relatively negligible effect on the impedance and phase angle measurements. The results therefore demonstrated that the process did not significantly alter the eddy current responses from the aluminum alloy blocks.

Figure 2:
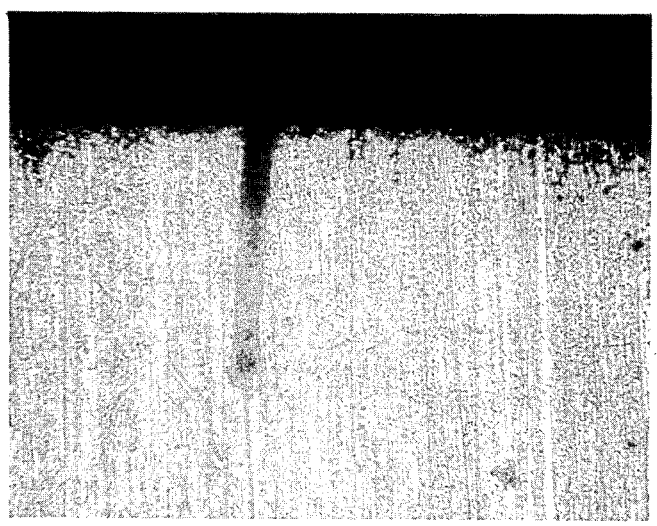
FIG. 2 is a photomicrograph of a cross-sectional view of another reference standard aluminum alloy block illustrating a slot indentation formed in accordance with the method of the subject invention, the slot indentation being magnified approximately 50X.

Notches were formed in the annealed 6061 aluminum alloy blocks by an indenting tool made from 200 $\mu$m (8 mil) shim stock. Details of the cracks formed in 6061 aluminum alloy blocks are depicted in the photomicrographs of FIGS. 1 and 2. Each notch produced by this tool required a compressive deformation force of on the order of about 80-100 kilopound (kip) to close each notch. Work on the 7075 aluminum alloy samples indicated that a comprehensive deformation force of a similar magnitude to that required to close the 6061 alloy notch was required to close each notch formed in this alloy. Such a large force can cause the block to buckle. However, it was found that block buckling could be reduced by machining the faces on which the compressive load was applied so as to make them substantially perpendicular to the applied load prior to block compression. It was also found that maintaining close tolerances on the surface of the block faces among each of the blocks helped to establish a greater degree of uniformity of closure at a particular load, thereby resulting in a greater degree of uniformity in the blocks that were produced in accordance with the foregoing method of the invention.

NOTCH MEASUREMENTS

All of the compressed notches and EDM notches were made with tools having a circular-shaped end having a radius of curvature of approximately 3.25 mm. Each notch had a length of approximately 3 mm and a depth of
approximately 1 mm, plus or minus 10%.

The change of the impedance ($\Delta Z$) measured from an eddy current probe as it traversed the surface of the specimen was used to determine the characteristic response to the presence of a flaw.

Impedance measurements were obtained from the probe while it was positioned over a flaw ("on-flaw") and when it was displaced from a flaw ("off-flaw"). The difference between the impedance vector measurement on the flaw and the impedance vector measurement off the flaw yields a change in impedance which is indicative of the presence of a flaw.

The foregoing impedances were measured using a uniform field probe operating at 2 MHz and with an unshielded, single coil ferrite core probe operating at 100 kHz. The measurements from the uniform field probe have been used successfully to calculate flaw depth using optical measurements of the width and length of a notch under study and the equations discussed below. With the ferrite core probe, a lift-off impedance was measured by positioning a 0.05 mm. thick insulating shim to produce a controlled displacement or "lift-off" of the probe end from the surface of the test block under the probe, which was on the block but off the flaw.

The impedance change produced by the movement of the probe away from the test piece ("lift-off" impedance) is a source of unwanted signal input (noise) during the inspection of parts for fatigue cracks. Many eddy current detection instruments are designed to electronically cancel any portion of a flaw signal that lies in the direction of the lift-off vector, thus making the inspections less susceptible to noise input and resultant misinterpretation. The data in Table II are intended to demonstrate that as the notch width increases, the resulting phase angle of the eddy current signal also increases for the conventional single coil ferrite core probe. The notch width is the distance perpendicular to the long axis of the notch, and the eddy current signal is the impedance change, or $\Delta Z$. The consequence of this relationship is shown in Table IV in the third column. As the notch width increases, the $\Delta Z$ phase increases and the angle between the lift-off signal (unwanted input) and the flaw signal decreases (separation angle in Table IV). This same phenomenon is also seen in the behavior of the uniform field probe, as is shown in the data in Table III. The implication is that as this separation angle becomes smaller, more of the flaw signal lies in the direction of the lift-off signal, and less of the flaw signal lies in the direction of detectability which is perpendicular to lift-off. Since fatigue cracks are usually very tightly closed, often to the point of being visually undetectable, calibration artifacts utilizing wide notches as fatigue crack simulations are unable to produce signal which accurately imitate signals from real fatigue cracks.

Figure 3:
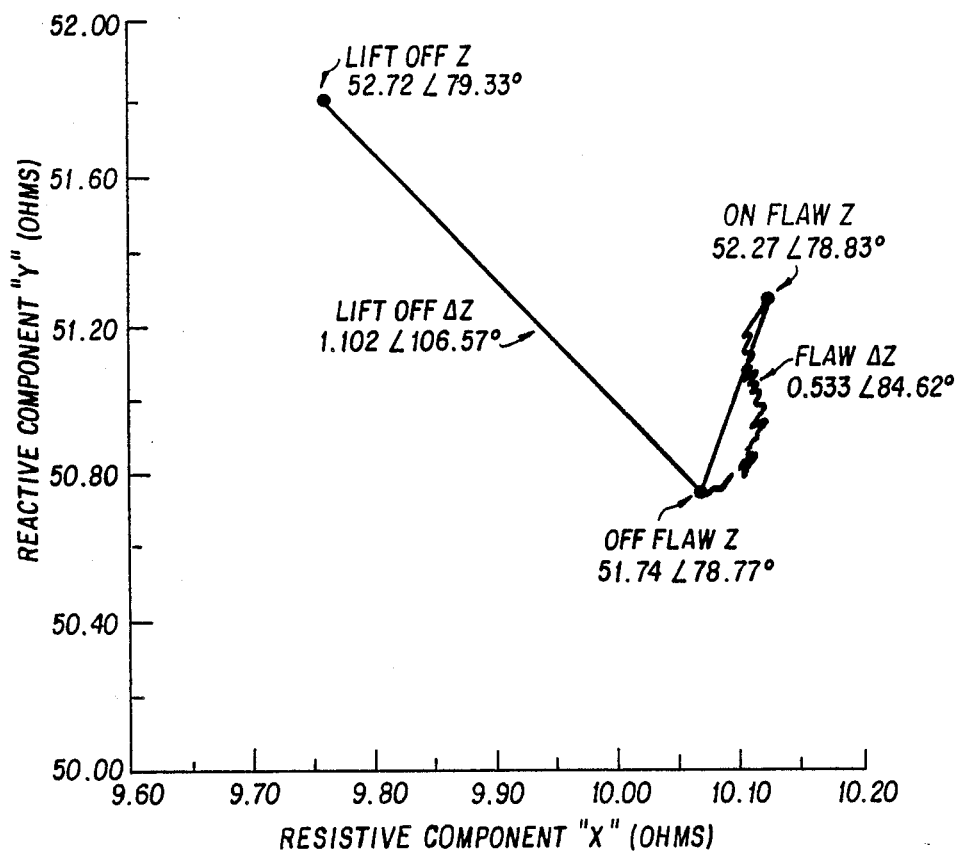
FIG. 3 is a graph of an eddy current probe output depicting the monitored electrical parameter change, $\Delta Z$, as the probe moves from an off-flaw position to an onflaw position.

FIG. 3 is an impedance plane plot of a typical data set showing the measured impedances and calculated vectors taken with the ferrite core probe. Because the instrument used with the eddy current probe for these measurements was capable of measuring both amplitude and phase angle differences, both a real and an imaginary component could be obtained from the test results. The real or resistive component is illustrated in the graph on the X axis and is labeled "RESISTIVE COMPONENT", and the imaginary component is listed on the Y axis as "REACTIVE COMPONENT".

The line drawn between the "Off Flaw Z" point and the "On Flaw Z" point represents a vector which is the calculated response as the probe passes from a portion of a specimen having no perceptible flaw formed therein to a portion of the specimen having a perceptible flaw. The curved, broken line extending between the two aboveidentified points represents the data collected from a test as the probe passed from a portion of the specimen which had no flaw to the portion of the specimen which did contain a flaw.

RESULTS

The 6061 aluminum alloy samples were not solution treated after processing, and thus did not return to their original temper. Nor were these samples subjected to hardness testing. However, the phase of the eddy current probe impedance data taken on these first samples did show a monotonic change with decreasing size of notch opening, as demonstrated in Table II below. While data for reference standard blocks having a notch width of from about 0.02 mm to about 0.08 mm (following block compression) are shown, the principles of the subject application are likewise applicable for blocks having notches which range from no perceptible width to a width of about 0.1 mm following block compression. Further, those samples with relatively wide notch openings yielded curves whose phases were closer to that of the "lift-off" vector, which is the line defined by the points "Lift Off Z" and "Off Flaw Z" in FIG. 3, whereas specimen blocks having closed or nearly closed notch openings yielded results similar to those shown in the curve line "Flaw $\Delta Z$" shown between the points "On Flaw Z" and "Off Flaw Z" in FIG. 3.

Measurements were also made on reference standards having indentations produced by an electrical discharge machining process (EDM) Because these EDM-produced indentations were similar to those used in current conventional practice, they were not compressed prior to evaluation The results that were obtained from the EDM-produced notches were tabulated and compared to reference standard blocks manufactured in accordance with the deformation process of the present invention. The EDM process produces notches having a notch width of generally no less than 0.10 mm, and therefore significantly larger than the notches produced in specimen using the compressed notch method of the present invention.

FIG. 3 illustrates that as the phase of $\Delta Z$ decreases, the separation angle between the on flaw vector and the lift-off vector becomes larger The separation angle represents the difference in the phase angle measured between the on-flaw impedance and the lift-off impedence. Similarly, if the phase of $\Delta Z$ for an EDM notch is compared to that of a fatigue crack or compressed notch of the subject invention, the fatigue crack will have a much larger separation angle with respect to the lift-off vector than will the EDM notch, as demonstrated by the data in Tables III and IV.

The relationship between $\Delta Z$ and notch width can be demonstrated in the formulation for $\Delta Z$ in the equation below for the case of a spatially uniform magnetic field, $$\Delta Z = \frac{c}{\sigma} \frac{H^2}{I^2} \left[ \Sigma + (1+i)\frac{c}{\delta}\Sigma^1 + i\frac{c\Delta u}{\delta^2}\Sigma^1 \right]$$

where $$\Sigma = -3 - 1.25\left[\frac{a}{c}\right] + 0.66\left[\frac{a}{c}\right]^2;$$

$$\Sigma^1 = -0.02 + 2.56\left[\frac{a}{c}\right] + 1.11\left[\frac{a}{c}\right]^2 - 1.70\left[\frac{a}{c}\right]^3;$$

$\sigma$ is the conductivity;
$\delta$ penetration depth of the induced current;
I is current (in amperes);
H is magnetic field strength (ampere per meter);
$\Delta u$ is the flaw width;
c is the flaw half-length;
a is the flaw depth and;
$a/\delta \gg 1$.

Because of assumptions made during the derivation of the above equation, this formulation is only valid when the ratio of $a/\delta$ is much greater than one. Since the frequency of current flow and depth of penetration of the eddy currents ($\delta$) are inversely proportional, a high frequency must be used with shallow flaws, i.e. where "a" is small. For this reason, we operated the uniform field probe at 2 MHz in the experiments reported here. Since the operation of the single coil ferrite core probe is not constrained by analytical assumptions, but rather by its electrical operating characteristics, we chose to operate this probe at the lower frequency of 100 KHz.

The data presented in Table III illustrates how the phase angle of $\Delta Z$ for the uniform field probe increases with increases in notch openings ($\Delta u$). Data from the ferrite core probe (Table IV) illustrates a similar trend. The data shown in Tables III and IV represent average values obtained from at least four scans.

TABLE II

| Ferrite Core Probe $\Delta Z$ Magnitude and Phase for Different Notch Openings in 6061 Aluminum Alloy Samples. | | |
|---|---|---|
| Notch Width (mm) | $\Delta Z$ (Mag. $\Omega$) | $\Delta Z$ Phase (°) |
| 0.02 | 0.47 | 73.89 |
| 0.05 | 0.47 | 76.55 |
| 0.08 | 0.48 | 77.99 |

TABLE III

Uniform Field Probe ΔZ Magnitude and
Phase on 7075-T6 Aluminum Alloy Samples.

| Notch Width (mm) | Z (Mag. Ω) | ΔZ Phase (°) |
|---|---|---|
| Compressed Notches | | |
| 0.025 | 0.636 | 49.14 |
| 0.080 | 1.274 | 67.94 |
| EDM Notches | | |
| 0.165 | 0.946 | 69.74 |
| 0.203 | 1.148 | 71.14 |

TABLE IV

ΔZ and Separation Angle between Lift-off
and Flaw Vectors on 7075-T6 Aluminum
Alloy Samples using Ferrite Core Probe.

| Notch Width (mm) | ΔZ (Mag. Ω) ∠ PH (°) | Separation Angle |
|---|---|---|
| Compressed Notches | | |
| 0.025 | 0.461 ∠ 81.13 | 25.92 |
| 0.050 | 0.470 ∠ 85.87 | 20.26 |
| 0.080 | 0.467 ∠ 86.96 | 19.14 |
| EDM Notches | | |
| 0.155 | 0.387 ∠ 91.64 | 15.40 |
| 0.165 | 0.358 ∠ 92.25 | 14.53 |
| 0.206 | 0.443 ∠ 92.18 | 14.57 |

From the foregoing data, it is apparent that the formation of compressed notches in aluminum alloy blocks provides a technique for making artifact standards for eddy current probe calibration prior to probe use in evaluating samples such as aircraft framework for the presence of structural flaws. The foregoing method solves many of the difficulties encountered when using conventional calibration procedures such as those involving relatively large EDM-produced notches or the controlled growth of fatigue cracks. As is evident from the tabular data, the angle between the lift-off vector and the flaw vector (designated "separation angle" in Table IV) is greater for compressed notches than it is for EDM notches. Graphically illustrated, as the notch width increases, the response from the blocks having an EDM notch more closely aligns with the lift-off vector, the line illustrated in FIG. 3 between the points "off flaw Z" and "lift off Z". As the notch width decreases, the eddy current probe response measured from blocks having a compressed notch more closely aligns with the flaw vector, the line illustrated in FIG. 3 between the points "off Flaw Z" and "on Flaw Z". In other words, the smaller the notch width, the more the response from the measurement resembled the line between the points "off Flaw Z" and "on Flaw Z".

As was stated earlier, many eddy current detection instruments are designed to electronically cancel any portion of the flaw signal that lies int he direction of the lift-off vector. Therefore, these data clearly indicate that the compressed notch samples made using the method of the present invention provide reliable and consistent calibration measurements indicative of a fatigue crack. The EDM notches, which are significantly larger in width than are the deformation-induced and compressed notches, yield results that are significantly different than those obtained from fatigue cracks that develop in structural framework.

Although the present invention has been described with reference to the various preferred embodiments, the invention is not solely limited to the detail set forth above. Other substitutions and modifications that may occur to those of ordinary skill in the art are intended to fall within the scope and spirit of the invention as set forth in the appended claims.

What is claimed is:

1. A method of manufacturing a reference standard block for use in nondestructive magnetic test probe calibration, the method comprising the steps of:
   (a) forming an indentation having a longitudinal axis of prescribed dimensions in a metal block, said indentation extending inwardly of said block from an opening formed in an outer surface of said block; and
   (b) compressing said block in a direction generally transverse of said longitudinal axis of said indentation with a force sufficient to substantially close said indentation opening, whereby the block is responsive to a magnetically induced eddy current to provide an indication incident to a nondestructive magnetic test probe calibration.

2. A method according to claim 1, further comprising the step of annealing said block.

3. A method according to claim 2, further comprising the step of heat treating said block.

4. A method according to claim 3, wherein said heat treating step is conducted subsequent to annealing.

5. A method according to claim 1, wherein said block is formed from an aluminum alloy.

6. A method according to claim 5, wherein said alloy is a tempered alloy.

7. A method according to claim 6, wherein said aluminum alloy is provided with a T6 temper.

8. A method according to claim 5, wherein said aluminum alloy is tempered following said step of block compression 9. A method according to claim 1, wherein said block indentation is formed by an indentation tool that is directed into physical engagement with said block.

10. A method according to claim 9, wherein said indentation tool is manipulated to form said block indentation of a length of from about 1 mm to about 20 mm.

11. A method according to claim 10, wherein said block is compressed to provide said indentation with a width of from about 0 005 mm to about 0.10 mm following block compression.

12. A method according to claim 1, wherein said block indentation is formed by electrical etching of said block.

13. A method according to claim 1, wherein said block is machined along opposed block sides so as to position the machined block sides substantially perpendicular to the direction of block compression 14. A reference standard block for calibrating nondestructive magnetic testing equipment, comprising a metallic material having a compressed indentation of prescribed dimensions and having a longitudinal axis formed by compressing said block in a direction generally transverse said longitudinal axis the block being responsive to a magnetically induced eddy current to provide an indication of the presence of the block indentation incident to nondestructive magnetic testing equipment calibration.

15. A reference standard block according to claim 14, wherein the block is formed from an aluminum alloy.

16. A reference standard block according to claim 15, wherein said aluminum alloy comprises Al:6061 or Al:7075.

17. A reference standard block according to claim 16, wherein said aluminum alloy is a tempered aluminum alloy.

18. A reference standard block according to claim 15, wherein said aluminum alloy is provided with a T6 temper.

19. A reference standard block according to claim 14, wherein said compressed indentation has a length of from about 1 mm to about 20 mm.

20. A reference standard block according to claim 14, wherein said compressed indentation has a width of from about 0.02 mm to about 0.10 mm.

* * * * *